(12) United States Patent
Wach et al.

(10) Patent No.: US 8,152,755 B1
(45) Date of Patent: Apr. 10, 2012

(54) SYSTEM AND METHOD FOR DELIVERING A THERAPEUTIC AGENT WITH FINESSE

(75) Inventors: Michael L. Wach, Alpharetta, GA (US); W. Robert Taylor, Stone Mountain, GA (US); Jack C. Griffis, III, Decatur, GA (US); Raymond P. Vito, Atlanta, GA (US)

(73) Assignee: Cell Precision LLC, Atlanta, GA (US)

( * ) Notice: Subject to any disclaimer, the term of this patent is extended or adjusted under 35 U.S.C. 154(b) by 0 days.

(21) Appl. No.: 12/731,019

(22) Filed: Mar. 24, 2010

(51) Int. Cl.
*A61M 37/00* (2006.01)
*A61M 31/00* (2006.01)

(52) U.S. Cl. .......................................... 604/83; 604/60

(58) Field of Classification Search .................... 604/18, 604/82–85, 518, 140, 144, 149, 150, 57–64
See application file for complete search history.

(56) References Cited

U.S. PATENT DOCUMENTS

| | | | | |
|---|---|---|---|---|
| 5,147,315 | A | * | 9/1992 | Weber ....................... 604/164.09 |
| 2002/0164310 | A1 | * | 11/2002 | Flugelman et al. ......... 424/93.21 |
| 2010/0262073 | A1 | * | 10/2010 | Henniges et al. ............... 604/82 |

* cited by examiner

*Primary Examiner* — Kevin C Sirmons
*Assistant Examiner* — Bradley Osinski
(74) *Attorney, Agent, or Firm* — Gardner Groff Greenwald & Villanueva, PC

(57) ABSTRACT

A catheter for delivering a therapeutic agent to a target site of a human or animal subject can include a substantially flexible and biocompatible catheter body having a proximal end and a distal end. An eductor can be located at the distal end of the catheter body, and a first lumen within the catheter body for housing the therapeutic agent can be in fluid communication with the eductor. A second lumen, also in fluid communication with the first lumen, can extend from the proximal end of the catheter body towards the eductor and can have an output port at the distal end of the catheter body. The eductor can be operable to induce the therapeutic agent to flow from the first lumen out of the output port in response to fluid flowing through the second lumen.

55 Claims, 9 Drawing Sheets

DETAIL G

SECTION A-A

DETAIL B

SECTION C-C

DETAIL D

SECTION F-F

DETAIL G

SYSTEM AND METHOD FOR DELIVERING A THERAPEUTIC AGENT WITH FINESSE

FIELD OF THE TECHNOLOGY

The present technology generally relates to a system and method for delivering one or more therapeutic agents, such as stem cells, progenitor cells, drugs, nanostructures carrying pharmaceutical payloads, etc., in a medical context, in which the one or more agents are carried in the distal, or active, end of a catheter or other the delivery system and emitted using an eductor, the Venturi effect, or flow-induced suction.

BACKGROUND

Certain medical treatments involve inserting a tube, such as a catheter, a needle, a cannula, an endoscope, etc., into a patient (e.g., a human or animal subject) and delivering a therapeutic agent to the patient via the tube. In some cases, the tube delivers the therapeutic agent for a systemic impact. For example, the therapeutic agent disperses throughout the patient's body to treat a disease likewise spread throughout the patient's body. In other cases, the tube delivers the therapeutic agent to a specific site that is diseased or that may otherwise need treatment. For example, such a site might be a diseased area of a heart, an artery, a vein, a lesion, or cardiovascular tissue that is ischemic or necrotic. In such instance, a practitioner positions the distal tip of the tube at the treatment site, for example at an area of the patient's heart, and injects a therapeutic agent into the proximal end of the tube located outside of the body. The therapeutic agent flows through the tube and into the target tissue. In other words, conventional catheters deliver therapeutic agents over a channel that extends from the proximal catheter end to the distal catheter end.

This conventional approach subjects the therapeutic agent to mechanical stress (e.g., shear stress) and other conditions that may be problematic as the agent flows through the catheter channel. While many conventional therapeutic agents are mechanically robust and can withstand such stress, cells (such as stem cells), certain particles, and certain other therapeutic agents (and potentially certain large molecule drugs) are sensitive to stress, and their therapeutic effectiveness can be impaired during flow through the channel. Studies show that these agents, unlike typical traditional therapeutic agents, can be affected in complex ways by biomechanical forces and environmental factors typically associated with their handling and, more significantly, with their delivery to an organ, organs or organ system(s) in need of treatment. Although these effects can dramatically influence therapeutic agent efficacy, insufficient attention has been paid to managing adverse forces and conditions incurred during delivery.

Delivery over a long catheter channel can cause problems even when shear stress is modest. A modest but sustained shear stress can subject a therapeutic agent to a significant, detrimental shear dose, for example. The term "shear dosing," as used herein, generally refers to the magnitude of shear (or shear stress or a related parameter) to which an agent is subjected, integrated over time of exposure. (For example, a shear dose may be computed as an integral of shear over time.) A catheter having a long delivery channel that subjects a therapeutic agent to modest shear over an extended period of time may produce a high shear dose that compromises therapeutic efficacy. Likewise, the impact of conditions other than shear can accumulate as an agent flows along an extended catheter channel.

SUMMARY

In certain example forms, the present invention relates to a system for delivery of a therapeutic agent to a target site of a human or animal subject. The system can deliver the therapeutic agent with finesse, for example reducing shear exposure or otherwise managing mechanical effects applied to the therapeutic agent during delivery. The system can include a generally elongate and flexible catheter having a proximal end, a distal end, and first and second lumens extending therethrough. The first and second lumens can be in fluid communication, each comprising an input port and an output port. The input port of the first lumen can be generally aligned with the output port of the second lumen at the distal end, and the output port of the first lumen can be generally aligned with the input port of the second lumen at the proximal end. The first lumen can define a reservoir for housing the therapeutic agent therein. A fluid source can be coupled to the input port of the second lumen. Fluid flow through the second lumen from the fluid source can induce the therapeutic agent to flow from the reservoir of the first lumen into the second lumen and out of the output port.

In another form, the present invention relates to a method for delivering a therapeutic agent to a target site of a human or animal subject. The method can include the steps of guiding a catheter housing the therapeutic agent therein to the target site and inducing or educing the therapeutic agent to flow from the chamber through the distal end of the catheter to the target site.

In yet another form, the present invention relates to a catheter for delivering a therapeutic agent to a target site of a human or animal subject. The catheter can have a substantially flexible and biocompatible catheter body with a proximal end and a distal end with an eductor. Within the catheter body can be first and second lumens. The first lumen, which can be in fluid communication with the eductor, can house the therapeutic agent near the distal end of the catheter body. The second lumen, which can be in fluid communication with the first lumen, can have an output port at the distal end of the catheter body. The eductor can be operable to induce the therapeutic agent to flow from the first lumen into the second lumen and out of the output port in response to fluid flowing through the second lumen.

In yet another form, the present invention relates to a method for delivering therapeutic cells. The method can include the steps of loading the therapeutic cells into a catheter through a port at a distal end of the catheter, disposing the distal end of the catheter in a vascular lumen of a patient, and emitting the loaded therapeutic cells out of the disposed distal end of the catheter and into the patient.

In yet another form, the present invention relates to a catheter. The catheter can include a reservoir, disposed at a distal end of the catheter, that is operable to contain a therapeutic agent, and an eductor coupled to the chamber and operable to draw the therapeutic agent out of the chamber for delivery to a patient.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of example embodiments of the invention, and are not restrictive of the invention, as claimed.

DETAILED DESCRIPTION OF EXAMPLE EMBODIMENTS

Figure 1:
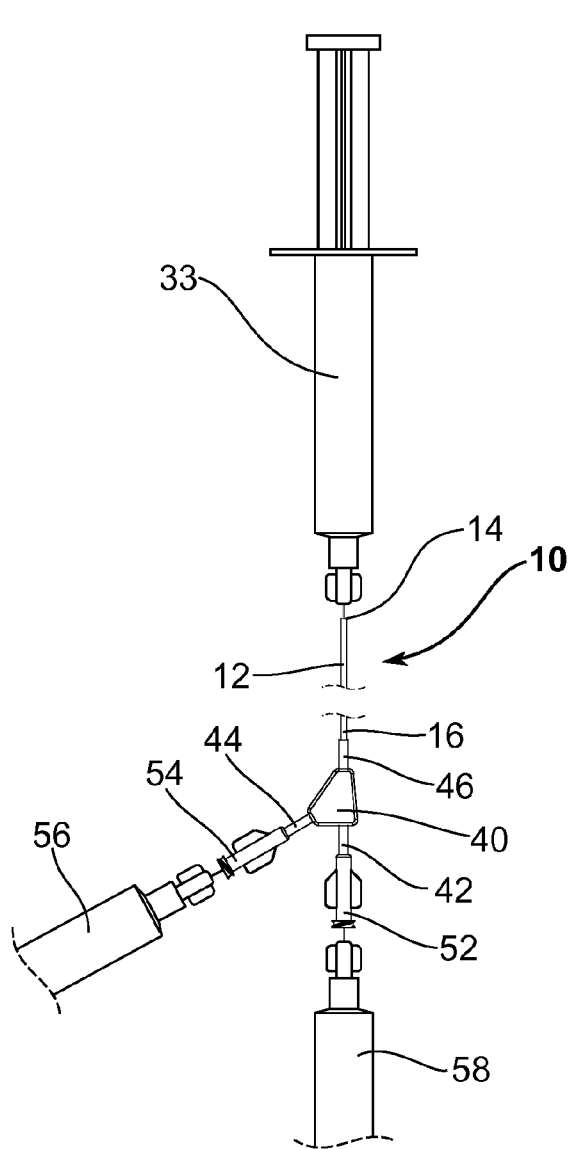
FIG. 1 shows a front view of a delivery catheter according to a first example embodiment and showing syringes inserted into a distal end and proximal end thereof.
Figure 2:
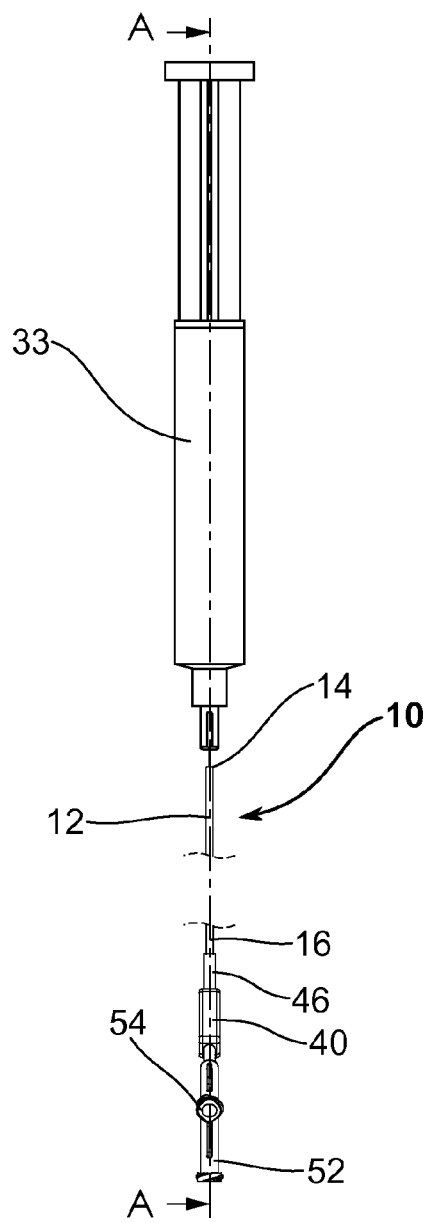
FIG. 2 shows a side view of the delivery catheter of FIG. 1 and showing a syringe inserted into the distal end thereof.
Figure 3:
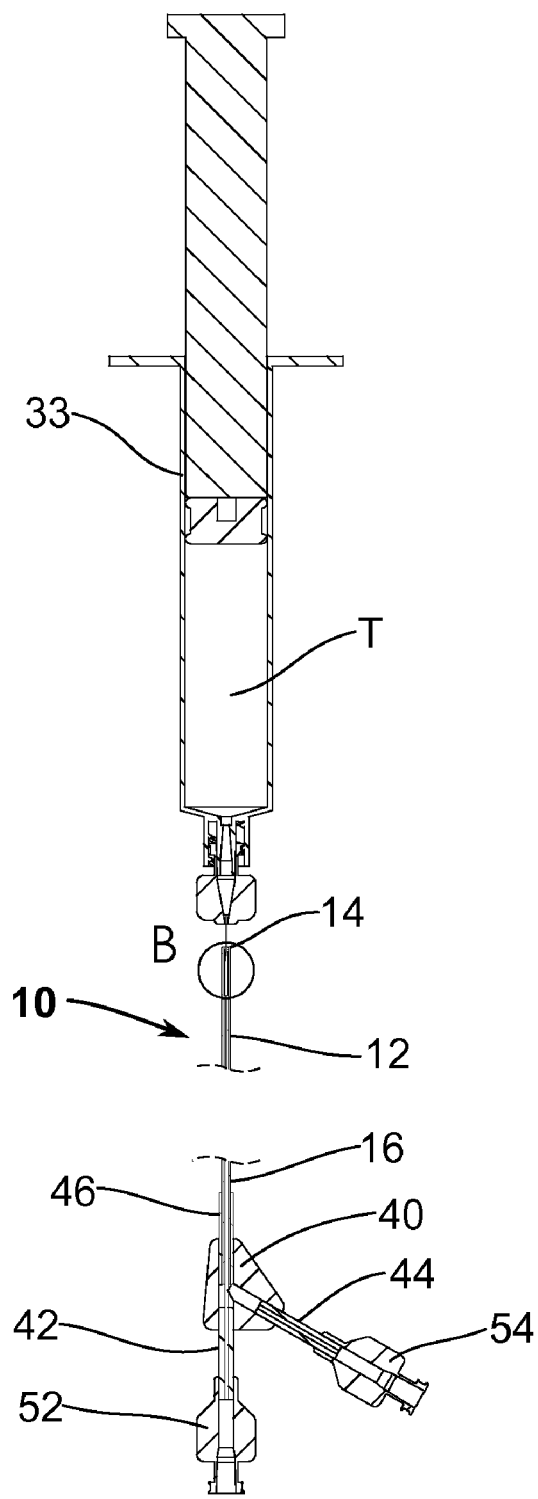
FIG. 3 shows a sectional view taken along line A-A of the delivery catheter and syringe of FIG. 2.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Referring now to FIGS. 1-7, a catheter 10 is shown according to a first example embodiment that supports reducing or managing shear exposure of a therapeutic agent during delivery to a target site (or addressing effects stemming from delivery and/or transportation over a catheter or other delivery channel). Those skilled in the art having benefit of this disclosure will appreciate that, beyond addressing shear exposure and the impact of other delivery conditions, the present technology and the catheter 10 address further needs in the art, for example providing delivery finesse even for therapeutic agents that are not susceptible to shear exposure.

The term "shear," as used herein, generally refers to: a force, movement, or pressure applied to a body perpendicular to a given axis, with greater force on one side of the axis than on the other side; lateral deformation produced in a body by an external force; a load, force, or system of forces producing a strain; the action on a body by a system of balanced forces whereby strain or deformation results; the internal resistance or reaction of a generally elastic body to external forces applied to the body; a stress applied parallel or tangential to a surface of a body; force acting on a fluid in a direction perpendicular to an extension of the fluid, like the pressure of air along the front of an airplane wing; or a strain that acts parallel to a face of a material upon which the strain acts. The term "shear," as used herein, generally encompasses shear force; shearing force; shear strain; shearing strain; shearing stress; shear stress; fluid shear stress; engineering shear strain; and average shear strain.

Those skilled in the art having benefit of this disclosure will appreciate that a viscous fluid (including air and water) moving along a solid boundary will incur shear adjacent the boundary. While the speed of the fluid at the boundary may approach zero, at some distance from the boundary, flow speed increases. (The region between two locations can be referred to as the boundary layer.) Thus, fluid velocity within a flow channel varies according to distance from a physical boundary. Such a change in velocity can produce shear stress.

Examples of therapeutic agents include vectors; living cells; therapeutic cells (stem cells, progenitor cells, cells having a capability to differentiate into a specific type of cell, or cells emitting or triggering emission of a healing biochemical after delivery into a patient in connection with a cell differentiation process); viruses having therapeutic potential; drugs; pharmaceutical agents; one or more pharmacologically active ingredients disposed in a delivery vehicle, a shell, or a casing; drug carrier systems; capsules containing drugs; biochemicals susceptible to various delivery conditions or forms of delivery stress; functionalized molecules; proteins; carbohydrate compounds and materials; small molecules compounds that may be sensitive to some aspect of delivery; and masses of cells that have begun to form into a tissue structure; nanostructures or other constructs (synthetic, biological, or some combination thereof) carrying pharmaceutical or cellular payloads, etc., without being exhaustive.

Figure 4:
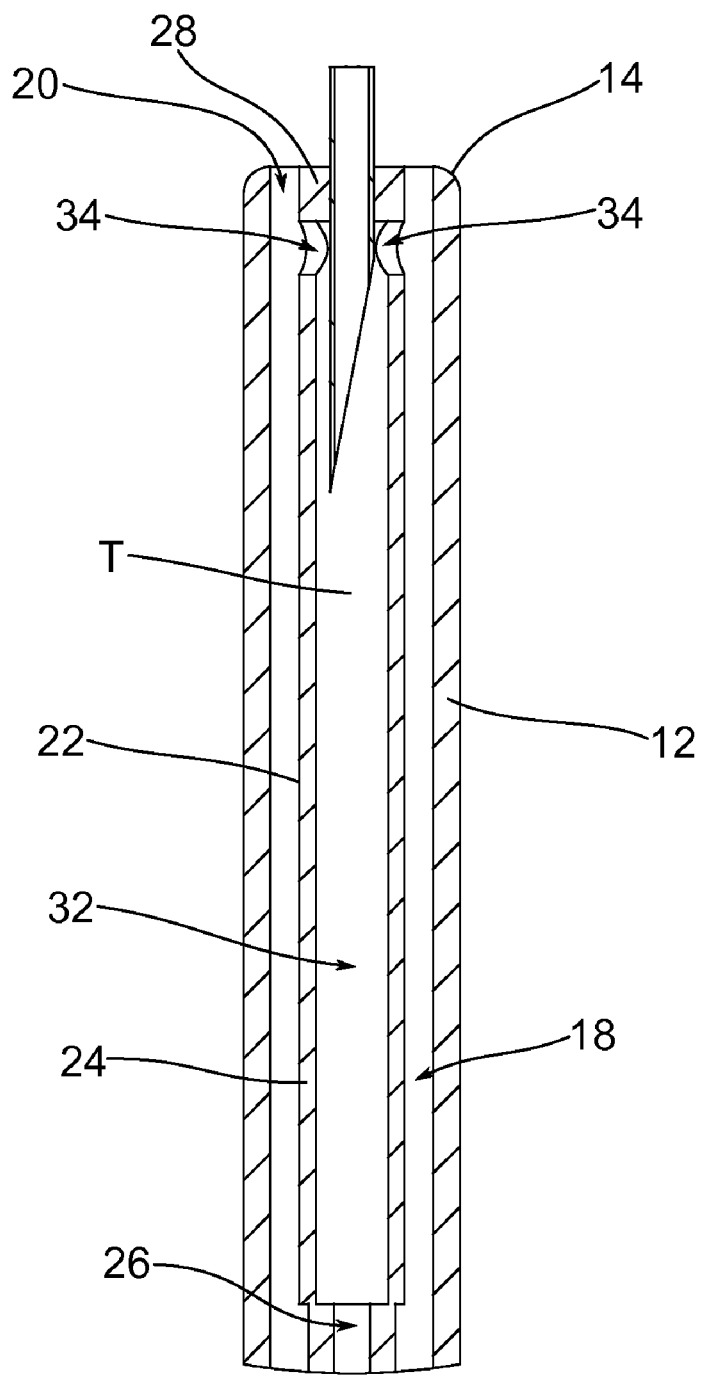
FIG. 4 shows a sectional view of a distal portion of the delivery catheter of FIG. 2.

The catheter 10 comprises an elongate outer tube or generally elongate cylindrical catheter body 12 having a distal tip or end 14, a proximal end 16, and a lumen 18 extending therethrough, as shown more clearly in FIG. 4. The body 12 can be constructed of a biocompatible and flexible material such as but not limited to silicone rubber latex, polyurethane, polyethylene, thermoplastic elastomers, or any other suitable polymer or material. The distal end 14 of the catheter body 12 includes an outer lumen fluid outlet port 20 at the end of the lumen 18. For certain applications, the catheter body can be sized for insertion into a vascular lumen of a human and/or for guiding lengthwise through the lumen during an intervention. The length of the catheter body is sufficient to reach the target site for therapeutic delivery, but can vary depending on application. For intravascular approaches, it is preferable to minimize the catheter outer diameter; however, diameters can also vary depending on application and approach. For similar cardiovascular access catheters, diameters can range from 3Fr (French, a measure of diameter in which 3 Fr=1 mm) up to 12Fr, and lengths are common up to 150 cm.

The catheter body 12 further includes an inner tube 22 placed coaxially within the lumen 18 of the cylindrical body 12. The inner tube 22 has a smaller diameter than the outer tube 12. The inner tube further includes a tube body 24 and an inner lumen 26. An inner lumen input port 28 is aligned with the outer lumen output port 20 and defines the entrance of the inner lumen 26. The inner lumen input port 28 includes a septum 30 that seals the end and prevents fluid flow therethrough. The septum 30 can be constructed of a penetrable, yet self-sealing material, such as thermoplastic elastomers, silicone, polyisoprene or other appropriate material.

The inner lumen 26 defines a therapeutic agent transport space, chamber or reservoir 32, which contains the therapeutic agent T during placement of the delivery catheter body 12 at the treatment site and protects the therapeutic agent T from adverse external forces encountered by the delivery catheter body 12 during placement at the treatment site. The portion of the inner tube 22 surrounding the transport space 32 can have a larger bore size than that of the inner lumen 26 to facilitate flow around the inner tube. In alternative embodiments, the bore sizes of the inner lumen 26 and the transport space 32 can be the same. Preferably, when the bore sizes of the inner lumen 26 and the transport space 32 are the same, a small piston can be placed within the transport space 32 and used to push out the therapeutic agent T from within the transport space 32. The piston can optionally be moved by a wire housed within the inner lumen that is attached to the piston. The wire can be manually or automatically manipulated and controlled at the proximal end of the catheter. Additionally, the piston can be moved by fluid pressure present within the inner tube 22. The inner lumen 26, the outer lumen 18, and the transport space 32 can be initially filled with a fluid such as, but not limited to, an inert gas or a liquid such as a saline solution, a radiographic solution, or other suitable solution or mixture.

A conventional syringe 33 of the type having a barrel that contains a fluid comprising a therapeutic agent T therein and a needle extending therefrom can be used to deliver the therapeutic agent to the transport space 32. Accordingly, the needle of the syringe 33 can penetrate the septum 30 and be inserted into the transport space 32 of the inner lumen 26. Syringes of the type having a plunger, barrel, and needle are generally well known, and hence the details of the syringe 33 are not discussed herein.

Proximate the septum 30 are one or more holes, apertures, or passageways 34 through the inner tube body 24 and around the circumference of the inner tube 22. The plurality of holes 34 permits the movement of fluid between the inner lumen 26 and the outer lumen 18. Accordingly, fluid in the inner lumen 26 can flow through the holes 34 and into the outer lumen 18. However, when the needle of the syringe 33 is inserted through the septum 30 to deliver the therapeutic agent into the transport space 32, the needle at least substantially, if not fully, occludes the holes 34 thereby preventing expulsion of fluid through the coaxial inner lumen 26. Additionally, the path through the holes 34 can optionally have a higher impedance to flow than the path through the inner lumen 26.

Referring back to FIGS. 1-3, the proximal end 16 of the catheter body 12 is attached to a hub or valve 40 having two syringe ports 42 and 44 and a catheter port 46. The valve 40 can be a Y-valve. The catheter port 46 is coupled to the proximal end 16 of the catheter body 12. An inner lumen syringe connector 52 is connected to the first syringe port 42 which is coupled to the inner lumen 26. An outer lumen syringe connector 54 is connected to the second syringe port 44 which is coupled to the outer lumen 18. The inner lumen syringe connector 52 and the outer lumen syringe connector 54 can be standard syringe connectors, such as luer-lock connectors though other non-standard connectors can be utilized such as quick-connects, luer slips or enteral only as appropriate to the application. Accordingly, the inner lumen connector 52 and the outer lumen connector 54 provide access channels to the inner lumen 26 and the outer lumen 18, respectively, and connection terminals for a syringe. The valve 40 and the syringe connectors 52, 54 can be constructed of plastics, polymers, metals, or any other suitable material.

Figure 5:
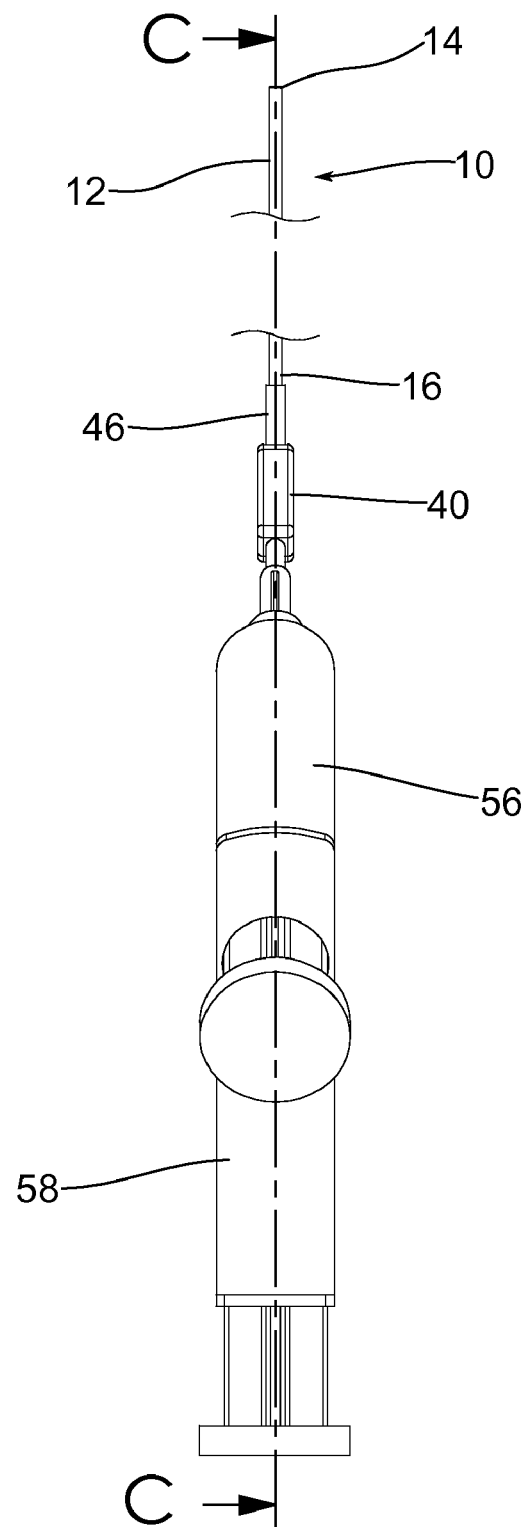
FIG. 5 shows a side view of the delivery catheter of FIG. 1 and showing a pressurizing syringe and a volume compensating syringe attached to its proximal end.
Figure 6:
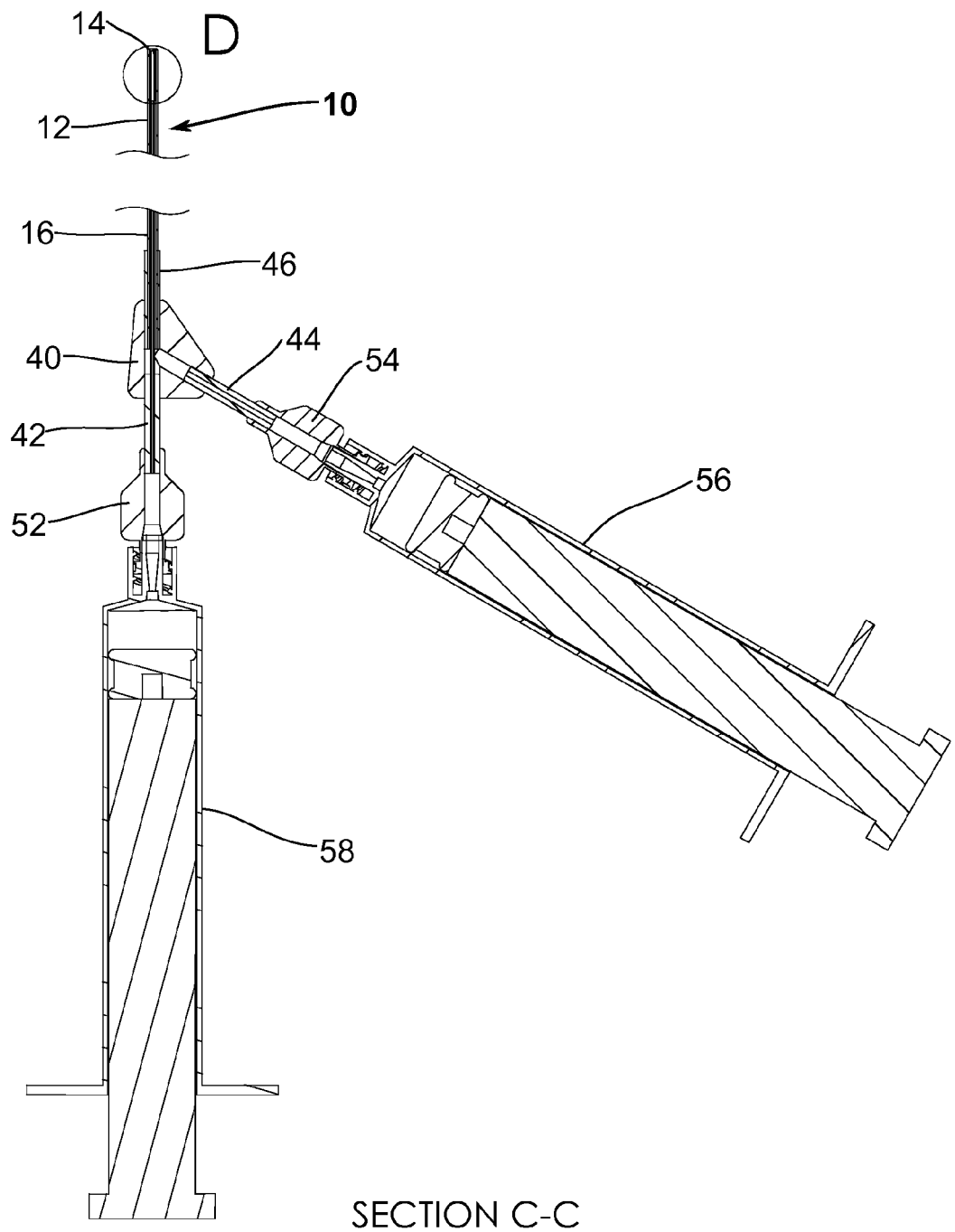
FIG. 6 shows a sectional view taken along line C-C of the delivery catheter and syringes of FIG. 5.
Figure 7:
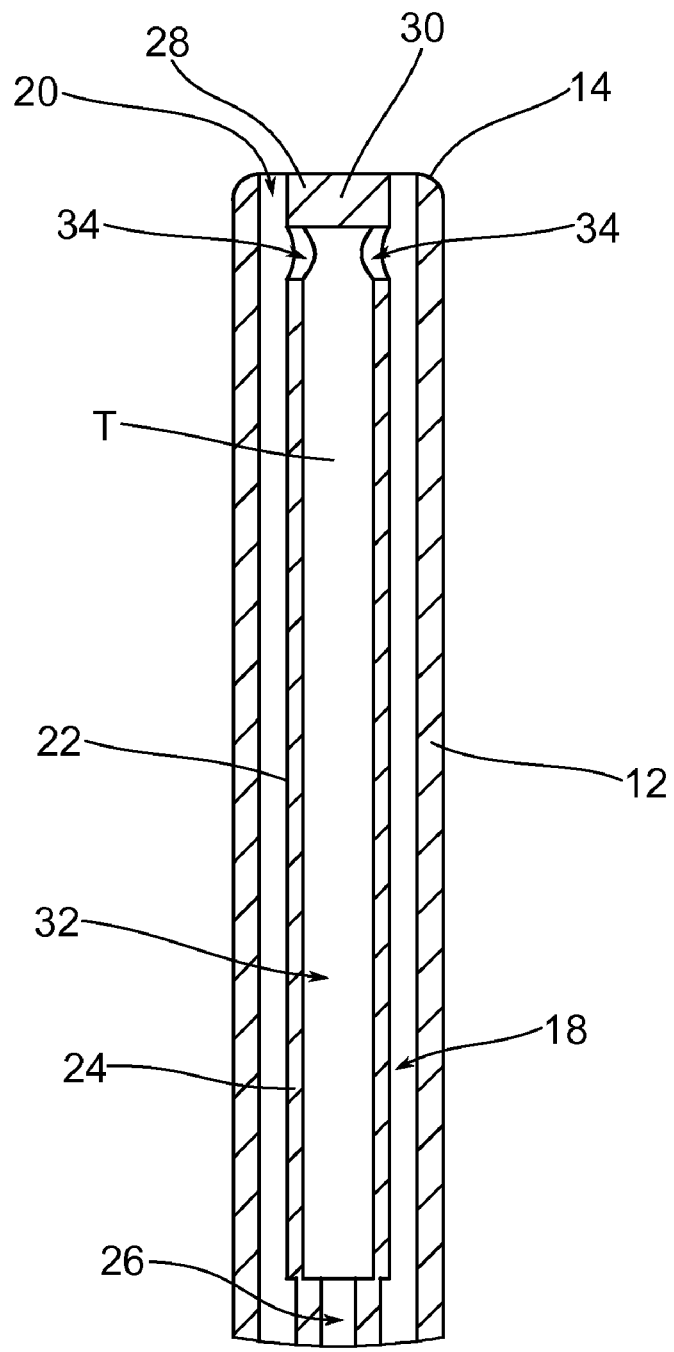
FIG. 7 shows a sectional view of the distal portion of the delivery catheter of FIG. 6 when the catheter is loaded with a therapeutic agent.
Figure 8:
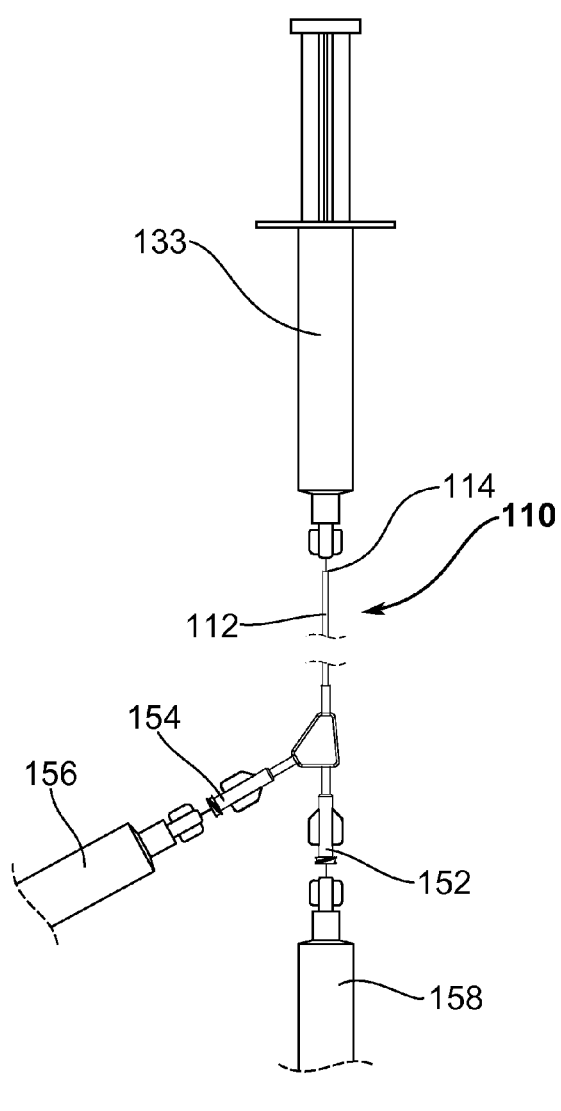
FIG. 8 shows a front view of a delivery catheter according to a second example embodiment and showing syringes inserted into a distal end and proximal end thereof.
Figure 9:
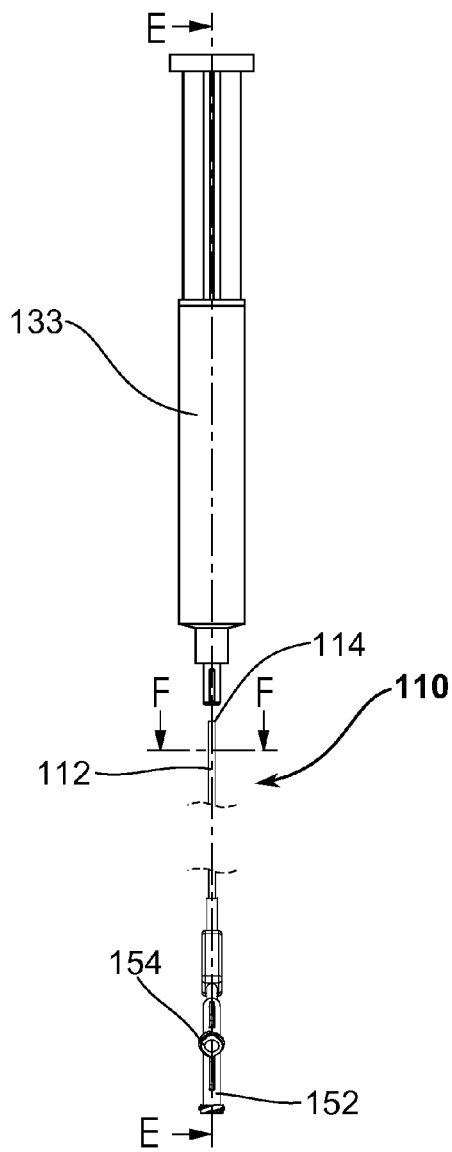
FIG. 9 shows a side view of the delivery catheter of FIG. 8 and showing a syringe inserted into the distal end thereof.
Figure 10:
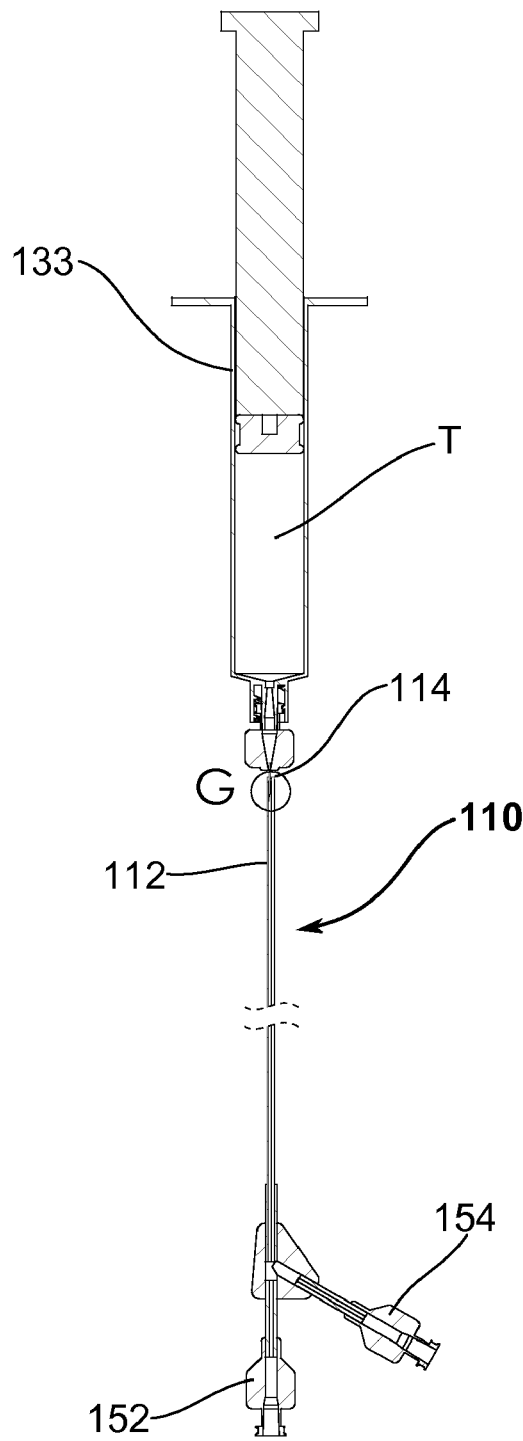
FIG. 10 shows a sectional view taken along line E-E of the delivery catheter and syringe of FIG. 9.
Figure 11:
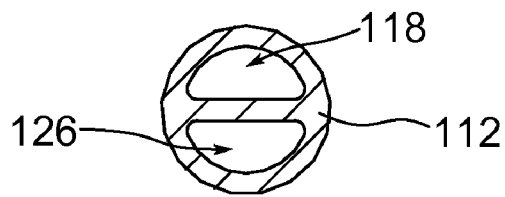
FIG. 11 shows a sectional view taken along line F-F of the delivery catheter of FIG. 9.

FIGS. 1, 5, and 6 show views of the catheter 10 with a pressurizing syringe 56 (or a fluid source) attached to the outer lumen connector 54 and a volume compensating syringe 58 (or a fluid regulator) attached to the inner lumen connector 52. The pressurizing syringe 56 contains a fluid, such as, but not limited to, an inert gas (e.g. $CO_2$ or Nitrogen) or a liquid such as a saline solution, radiographic solution, or other suitable solution or mixture. The volume compensating syringe 58 can be empty or contain some other low viscous biocompatible or bio-inert solution intended to compensate the volumetric changes that occur in the lumen containing the therapeutic agent T. In alternative embodiments, other fluid sources or fluid regulators for housing fluids can be used in lieu of the syringes 56 and 58.

In use, a practitioner couples the volume compensating syringe 58 to the inner lumen syringe connector 52 and the pressurizing syringe 56 to the outer lumen syringe connector 52. The practitioner also inserts the syringe 33 filled with the desired therapeutic agent into the distal tip 14 of the catheter 10 through the septum 30 of the inner lumen input port 28. The practitioner presses the plunger of the syringe 33 to displace the therapeutic agent T from the barrel of the syringe 33 into the transport space 32. To adjust for the change in fluid volume the inner lumen 26 experiences when the therapeutic agent T is released into the transport space 32, the plunger of the compensating syringe 58 alters its position within the syringe's barrel to adjust the fluid volume within the inner lumen 26 to thereby keep the therapeutic agent T within the transport space 32. After the therapeutic agent T has been fully displaced into the transport space 32, the needle of the syringe 33 is withdrawn from the catheter 10. The septum 30 reseals itself after the needle is withdrawn, thereby acting as a gate to prevent the implanted therapeutic agent T from leaking through the inner lumen input port 28.

The catheter 10 is now in a "loaded state," meaning it is ready to be positioned at a delivery site of a human or animal subject and used to deliver the therapeutic agent T thereto. For example, the catheter 10, with the therapeutic agent T loaded at its distal end 14, can be inserted through a guide needle or introducer sheath that is positioned at the target site of the human or animal subject. Once the distal end 14 of the catheter is positioned at the target delivery site, the practitioner depresses the plunger of the pressurizing syringe 56 to deliver the therapeutic agent T with the fluid in the pressurizing syringe. When the pressurizing syringe 56 is plunged, the fluid within the barrel of the syringe 56 is pushed into the outer lumen 18. As the fluid is pressurized, the fluid within the outer lumen 18 near the outer lumen outlet port 20 experiences the Venturi effect, thereby undergoing a reduction in fluid pressure near that region of the outer lumen 18. This reduction in pressure then pulls or draw the therapeutic agent T within the transport space 32 through the plurality of internal passageways 34 and into fluid of the outer lumen 18 in order to equalize the pressure in that region. The change in fluid volume when the therapeutic agent T is extracted from the transport space 32 can be compensated by the adjusting movement of a plunger in the compensating syringe 58 that is connected to the inner lumen syringe connector 52. Alternatively, a second pressurizing syringe can be attached to the inner lumen syringe connector 52 and plunged, in optional conjunction with the first pressurizing syringe 56, in order to advance, push out, or encourage flow of the therapeutic agent T.

As a second alternative (not illustrated), the transport space 32 (or some other chamber, container, or reservoir for holding the therapeutic agent T) can be confined to the distal end 14 of the catheter 10, without having the inner lumen 26 extend all the way to the proximal end 16 of the catheter 10. For this alternative, the therapeutic agent T can be loaded into the catheter 10 via inserting into the distal end 14 of the catheter 10 a cartridge that has already been filled with the therapeutic agent T. To relieve pressure, the proximal end of the transport space 32 (or the cartridge itself) can have one or more pressure-relief fluid connections to the outer lumen 18. With the internal passageways 34 sized appropriately, the pressure forces at the internal passageways 34 can be decreased below any pressure forces that may be present at the pressure-relief fluid connections. Accordingly, while fluid flow through the outer lumen 18 draws the therapeutic agent T into the outer lumen 18 for patient delivery, some fluid flows from the outer lumen 18 into the proximal end of the transport space 32 to compensate for departure of the therapeutic agent T from the transport space 32.

The holes 34 and other catheter dimensions may be sized appropriately using established design principles. For example, a computational fluid dynamic computer model of the catheter can be generated based on dimensions and tolerances selected. The model could benefit from any number of available software packages, such as Fluent (ANSYS Inc., Ann Arbor Mich.), available for computational fluid dynamic modeling. The model can predict, for example, the flow of the agent T for specified flows in the outer lumen 18. The flow of the agent predicted can be compared to the flow specified as needed or desired and the process repeated. Such iterative approaches to design are familiar to those familiar with design principals and/or skilled in the art of computational fluid dynamics. Ultimate in-vitro and other testing of the design is then used to validate the computational model.

Referring to the illustrated embodiment, the therapeutic agent T is transferred to the delivery site, typically undergoing relatively little or minimal shear stress as it travels from the transport space 32 to the delivery site. (However, in certain embodiments, shear stress may be controlled to a target level rather than minimized, for example in connection with achieving a prescribed shear dose.) Thus, the outer lumen 18 near the distal end 14 and associated passageways 34 provide an eductor to induce or educe flow of the therapeutic agent T from the transport space 32 to the delivery site. The eductor is further operable to mix the therapeutic agent from the first lumen with the fluid flowing through the second lumen. The eductor of the catheter 10 can use kinetic energy of a fluid flowing in the outer lumen 18 to entrain the therapeutic agent T, mix the therapeutic agent with that fluid, and deliver the mixture. Accordingly, the catheter 10 can deliver the therapeutic agent T with an extremely high level of finesse and without undue mechanical stress since the distance the therapeutic agent T travels to exit the distal end of the catheter 10 is small.

A delivery catheter 110 according to a second example embodiment of the present invention is shown in FIGS. 8-12. The catheter 110 is substantially similar to the catheter 10 of the first example embodiment but with the exceptions noted herein. Rather than including coaxial lumens, the catheter 110 includes a catheter body 112 having two semi-circular lumens 118, 126 in a double-D configuration extending therethrough. Separating the two lumens is a partition wall 122 that bisects the generally cylindrical catheter body 112, as shown more clearly in FIG. 11.

Figure 12:
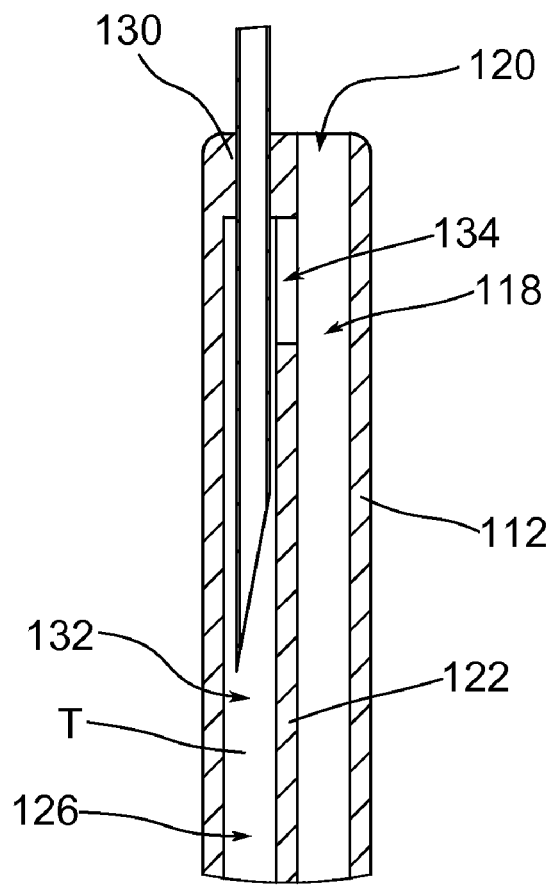
FIG. 12 shows a sectional view of a distal portion of the delivery catheter of FIG. 10.

FIG. 12 shows a sectional view of the distal end 114 of the catheter body 112. The distal end 114 of the catheter body 112 comprises a septum 130 proximate a lumen outlet port 120 of the first lumen 118. The septum 130 can be integral with the catheter body 112 or it can be a separate component permanently affixed to the catheter body 112. At least one internal passage or channel 134 couples the two lumens 118, 126 in fluid communication. The at least one channel 134 is substantially or completely occluded when the delivery needle of a syringe 133 is inserted into the second lumen 126. A transport space, chamber or reservoir 132 is defined by the second lumen 126. The transport space 132 is generally defined as a portion of the second lumen 126 that is located near the distal end of the catheter 110. In other embodiments, the second lumen 126 can have a different or similar bore or cross-sectional size as the transport space 132.

In use, the catheter 110 is loaded and manipulated in a manner similar to that of the catheter 10. A practitioner couples a pressurizing syringe 156 to a first lumen syringe connector 154 and a volume compensating syringe 158 to a second lumen syringe connector 152. The practitioner also inserts a syringe 133 filled with the desired therapeutic agent T into the distal tip of the catheter body 112 and through the septum 130 of the second lumen 126. The practitioner presses the plunger of the syringe 133 to displace the therapeutic agent T from the barrel of the syringe 133 into the transport space 132. The needle of the syringe 133 occludes the at least one internal channel 134 when the catheter 110 is being loaded, such that the therapeutic agent T is deposited solely into the transport space 132 of the second lumen 126. To adjust for the increase in fluid volume the inner lumen 126 experiences when the therapeutic agent T is released into the transport space 132, the plunger of the compensating syringe 158 alters its position within the syringe's barrel to equalize the fluid volume within the second lumen 126 to thereby keep the therapeutic agent T within transport space 132. After the therapeutic agent T has been fully displaced into the transport space 132, the needle can be withdrawn from the catheter body 112. The septum 130 reseals itself after the needle is withdrawn, thereby acting as a gate to prevent the implanted therapeutic agent T from leaking out.

The catheter 110 is now in a "loaded state," meaning it is ready to be positioned at a delivery site of a human or animal subject and used to deliver the agent thereto. For example, the catheter 110, with the therapeutic agent T loaded at its distal end 114, can be inserted through a guide needle or introducer sheath that is positioned at the target site of the human or animal subject. To deliver the therapeutic agent T to the target site, the practitioner depresses the plunger of the pressurizing syringe 156. When the pressurizing syringe 156 is plunged, the fluid within the barrel of the syringe 156 is pushed into the first lumen 118. As the fluid is pressurized, the fluid within the first lumen 118 near the lumen outlet 120 experiences the Venturi effect, resulting in lowered fluid pressure near the at least one internal passage 134 through which the therapeutic agent T is extracted in order to equalize the pressure in that region. The change in fluid volume when the therapeutic agent T is extracted from the transport space 132 is compensated by the adjusting movement of a plunger in the compensating syringe 158 that is connected to the second lumen syringe connector 152. Alternatively, a second pressurizing syringe can be attached to the second lumen syringe connector 152 and plunged, in optional conjunction with the first pressurizing syringe, in order to push the therapeutic agent T out of the transport space 132 and through the outlet port 120. The therapeutic agent T is thereby transferred to the delivery site, undergoing relatively little or minimal shear stress as it travels from the transport space 132 to the delivery site. Thus, the first lumen 118 near the distal end 114 and the associated at least one internal passage or channel 134 act as an eductor to induce flow of the therapeutic agent T from the transport space 132 and mix the therapeutic agent with the fluid in the first lumen 118. The eductor further induces the mixture of the therapeutic agent and fluid through the outlet port and into the delivery site. Accordingly, the catheter 110 can deliver the therapeutic agent T with an extremely high level of finesse and without undue mechanical stress because the distance the therapeutic agent T travels to exit the catheter is small.

Advantageously, the catheters of the present invention can be utilized to contain high volume fraction therapeutic cells and/or high viscosity therapeutic agents within the distal tip for transport intravascularly and for delivery directly to the target treatment site of a human or animal subject. This approach allows for the expulsion of the therapeutic cells from the delivery catheter with minimal shear stress on the cells, forces that could adversely impact their therapeutic efficacy. Furthermore, shortening the path length that a therapeutic agent travels during catheter-based delivery can reduce time of exposure to other transport conditions associated with delivery. Such catheters can be used to deliver therapeutic agents to treat diseased tissue or deliver therapeutic agents that are dispersed throughout the subject's body to treat a disease likewise spread throughout the subject's body.

While the invention has been described with reference to example embodiments, it will be understood by those skilled in the art that a variety of modifications, additions and deletions are within the scope of the invention, as defined by the following claims.

We claim:

1. A method for delivering therapeutic cells, comprising the steps of:
   loading the therapeutic cells into a catheter disposed outside of a patient through a port at a distal end of the catheter;
   disposing the distal end of the catheter lengthwise in a vascular lumen of the patient; and
   emitting the loaded therapeutic cells out of the disposed distal end of the catheter and into the patient,
   wherein the emitting step comprises suctioning the loaded therapeutic cells into a fluid stream.

2. The method of claim 1, wherein an eductor suctions the loaded therapeutic cells into the fluid stream.

3. The method of claim 1, wherein the catheter comprises an eductor disposed at the distal end.

4. The method of claim 1, wherein the emitting step comprises applying the Venturi effect to the loaded therapeutic cells.

5. The method of claim 1, wherein suctioning the loaded therapeutic cells into the fluid stream comprises applying flow-induced suction to the loaded therapeutic cells.

6. The method of claim 1, wherein the therapeutic cells comprise stem cells, progenitor cells, cells having a capability to differentiate into a specific type of cell, or cells emitting or triggering emission of a healing biochemical after delivery into the patient in connection with a cell differentiation process.

7. The method of claim 1, wherein the therapeutic cells comprise stem cells.

8. The method of claim 1, wherein the therapeutic cells substantially consist of stem cells.

9. The method of claim 1, wherein the therapeutic cells comprise progenitor cells.

10. The method of claim 1, wherein the therapeutic cells substantially consist of progenitor cells.

11. The method of claim 1, wherein the therapeutic cells comprise cells having a capability to differentiate into a specific type of cell.

12. The method of claim 1, wherein the therapeutic cells substantially consist of cells having a capability to differentiate into a specific type of cell.

13. The method of claim 1, wherein the therapeutic cells comprise cells emitting a healing biochemical after delivery into the patient in connection with a cell differentiation process.

14. The method of claim 1, wherein the therapeutic cells substantially consist of cells emitting a healing biochemical after delivery into the patient in connection with a cell differentiation process.

15. The method of claim 1, wherein the therapeutic cells comprise cells triggering emission of a healing biochemical after delivery into the patient in connection with a cell differentiation process.

16. The method of claim 1, wherein the therapeutic cells substantially consist of cells triggering emission of a healing biochemical after delivery into the patient in connection with a cell differentiation process.

17. The method of claim 1, wherein the loading step comprises piercing a distally located septum of the catheter that comprises a self-sealing material.

18. The method of claim 1, wherein the emitting step comprises entraining the therapeutic cells using kinetic energy of the fluid stream, mixing the therapeutic cells with the fluid stream to form a mixture, and delivering the mixture to the patient.

19. The method of claim 1, wherein disposing the distal end of the catheter lengthwise in the vascular lumen of the patient comprises guiding the catheter through the vascular lumen of the patient.

20. The method of claim 1, wherein the emitting step comprises inducing the therapeutic cells to flow from a first lumen of the catheter to a second lumen of the catheter, wherein the first and second lumens are coaxial, and wherein the fluid stream comprises fluid flowing through the second lumen.

21. The method of claim 1, wherein the emitting step comprises inducing the therapeutic cells to flow from a first lumen of the catheter to a second lumen of the catheter, wherein the first and second lumens are arranged in a double-D configuration, and wherein the fluid stream comprises fluid flowing through the second lumen.

22. The method of claim 1, wherein the emitting step comprises reducing shear exposure on the therapeutic cells during delivery.

23. The method of claim 1, wherein the emitting step comprises delivering the therapeutic cells while managing mechanical effects applied to the therapeutic cells.

24. The method of claim 1, wherein the loading step comprises loading the therapeutic cells into a distally disposed reservoir of the catheter.

25. The method of claim 1, wherein the catheter has a diameter between about three and twelve French.

26. A method for delivering therapeutic cells, comprising the steps of:
   loading the therapeutic cells into a catheter through a port at a distal end of the catheter;
   disposing the distal end of the catheter in a vascular lumen of a patient; and emitting the loaded therapeutic cells out of the disposed distal end of the catheter and into the patient, wherein the step of emitting the loaded therapeutic cells comprises drawing the loaded therapeutic cells from a chamber towards the distal end using the Venturi effect.

27. The method of claim 26, wherein an eductor suctions the loaded therapeutic cells into a fluid stream.

28. The method of claim 26, wherein the catheter comprises an eductor disposed at the distal end.

29. The method of claim 26, wherein an eductor applies the Venturi effect to the loaded therapeutic cells.

30. The method of claim 26, wherein a fluid stream creates the Venturi effect.

31. The method of claim 26, wherein the therapeutic cells comprise cells selected from the group consisting of stem cells, progenitor cells, cells having a capability to differentiate into a specific type of cell, and cells emitting or triggering emission of a healing biochemical after patient delivery in connection with a cell differentiation process.

32. The method of claim 26, wherein the therapeutic cells comprise stem cells.

33. The method of claim 26, wherein the therapeutic cells substantially consist of stem cells.

34. The method of claim 26, wherein the therapeutic cells comprise progenitor cells.

35. The method of claim 26, wherein the therapeutic cells substantially consist of progenitor cells.

36. The method of claim 26, wherein the therapeutic cells comprise cells having a capability to differentiate into a specific type of cell.

37. The method of claim 26, wherein the therapeutic cells substantially consist of cells having a capability to differentiate into a specific type of cell.

38. The method of claim 26, wherein the therapeutic cells comprise cells emitting a healing biochemical after delivery into the patient in connection with a cell differentiation process.

39. The method of claim 26, wherein the therapeutic cells substantially consist of cells emitting a healing biochemical after delivery into the patient in connection with a cell differentiation process.

40. The method of claim 26, wherein the therapeutic cells comprise cells that trigger emission of a healing biochemical after delivery in connection with a cell differentiation process.

41. The method of claim 26, wherein the therapeutic cells substantially consist of cells that trigger emission of a healing biochemical after delivery in connection with a cell differentiation process.

42. The method of claim 26, wherein the loading step comprises piercing a distally located septum of the catheter with a needle.

43. The method of claim 26, wherein the emitting step comprises entraining the therapeutic cells using kinetic energy of a fluid stream and mixing the therapeutic cells with the fluid stream.

44. The method of claim 26, wherein disposing the distal end of the catheter in the vascular lumen of the patient comprises guiding the catheter through the vascular lumen of the patient.

45. The method of claim 26, wherein the emitting step comprises causing the therapeutic cells to flow from a first lumen of the catheter to a second lumen of the catheter, and wherein the first and second lumens are coaxial.

46. The method of claim 26, wherein the emitting step comprises causing the therapeutic cells to flow from a first lumen of the catheter to a second lumen of the catheter, and wherein the first and second lumens are arranged in a double-D configuration.

47. The method of claim 26, wherein the emitting step comprises the therapeutic cells flowing from a first lumen of the catheter to a second lumen of the catheter that runs alongside the first lumen.

48. The method of claim 26, wherein the Venturi effect reduces shear exposure on the therapeutic cells.

49. The method of claim 26, wherein the emitting step comprises delivering the therapeutic cells while managing mechanical effects applied to the therapeutic cells.

50. The method of claim 26, wherein the chamber is disposed at the distal end of the catheter.

51. The method of claim 26, wherein the catheter has a diameter between three and twelve French.

52. The method of claim 26, wherein disposing the catheter comprises disposing the catheter lengthwise in the vascular lumen.

53. The method of claim 26, further comprising the step of
as the loaded therapeutic cells emit from the chamber, compensating for reduction in volume of the chamber occupied by the loaded therapeutic cells.

54. A system for delivering therapeutic cells, comprising:
a means for loading the therapeutic cells into a catheter disposed outside of a patient through a port at a distal end of the catheter;
a means for disposing the distal end of the catheter lengthwise in a vascular lumen of the patient; and
a means for emitting the loaded therapeutic cells out of the disposed distal end of the catheter and into the patient via suctioning the therapeutic cells into a fluid stream.

55. A system for delivering therapeutic cells, comprising:
means for loading the therapeutic cells into a catheter through a port at a distal end of the catheter;
means for disposing the distal end of the catheter in a vascular lumen of a patient; and
means for emitting the loaded therapeutic cells out of the disposed distal end of the catheter and into the patient via drawing the loaded therapeutic cells from a chamber towards the distal end using the Venturi effect.

* * * * *